United States Patent [19]

Amate

[11] Patent Number: Plant 7,297

[45] Date of Patent: Aug. 14, 1990

[54] *AGAPANTHUS ELLAMAE* PLANT

[76] Inventor: Archie A. Amate, 15662 Sunflower La., Huntington Beach, Calif. 92647

[21] Appl. No.: 313,549

[22] Filed: Feb. 21, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Francis X. LoJacono

[57] ABSTRACT

An *Agapanthus ellamae* plant which is defined by its exceptional vigor and having large heads of dark blue-violet flowers on scapes well exceeding the relatively compact foliage and, when in flower, will reach an overall height of 14.3 dm, which is taller than commonly found in other types of agapanthus plants, with numerous leaves that are united at the base into a short pseudo-stem with the leaves being formed having closely spaced veins about 2 mm apart near the center of the leaves which are thick-textured but pliable and reach a maximum length of 6.5 dm having a width of 4 to 5 cm.

2 Drawing Sheets

The present invention relates specifically to a new and distinct variety of the Agapanthus plant family. This new cultivar is known as an *Agapanthus ellamae* and was discovered by me as a seedling having the possible outcrossed parentage involving *A. africanus* and *A. praecox* ssp. orientalis. However, the seed and pollen parents can not be identified with certainty. It was discovered by me in 1978 among a group of cultivated plants, and at which time various seedlings were selected from crosses of hybrid seedling plants from which I hoped to develop a stock of commercial plants suitable for propagation and sale in the United States. The present plant has been successfully asexually reproduced by me, through the means of using tissue culture from the selected seedling under appropriate conditions at the Twyford Laboratories in Santa Paula, Calif. The present variety has been asexually reproduced during the last ten years since its discovery, and these asexual reproductions have continuously exhibited the following characteristics which clearly show that the new variety is stable.

My new and distinct cultivar, which will hereinafter be known as *Agapanthus ellamae,* is readily distinguishable from other Agapanthus cultivars and was suprisingly found to have exceptional vigor in its larger than normal, dark blue-violet flowers on scapes well exceeding the relatively compact foliage and dense floral arrangement of large bouquet-like inflorescense, with elongated leaves arranged disticously on a stem in two diametrically opposite rows, wherein each leaf blade is formed having closely spaced veins near the center of the blade and become progressively more closely spaced toward the margins thereof. Under closer observation of this unusual Agapanthus plant, that developed from the tissue culture thereof, it appeared to be quite different from all the other surrounding Agapanthus plants. That is, the present plant is relatively taller in comparison to the general Agapanthus in that it will reach between 12 to 14.3 dm in height with the leaves having a lighter green color (Green Group 143 of the R.H.S. Colour Chart). Thus, with continued close observations of this unique plant and asexual progeny thereof, I was convinced that it represented a new and distinct variety unlike any other plant formerly known to me or previously reported or described in published literature, as evidenced by the combination of features which are outstanding in my new plant.

There are two accompanying drawings present in the form of full color photographs, one of which is employed to show overall view thereof wherein the extra long stems are defined having larger than normal, dark blue-violet flowers (Violet-Blue Group 93A) on scapes that well exceed the relatively compact distichous foliage, One of the photographs shows the dense floral arrangement of the large bouquet-like inflorescence which is defined by larger than normal, dark blue-violet flowers.

In the following description of the plant, the color names and numbers used in describing the plant are taken from The Royal Horticultural Society Colour Chart.

THE PLANT

General characteristics: The plant is an evergreen perennial herb with thick, heavy rhizomes forming clumps by offsets.

Dimensions: When in flower, the plant may reach a height of 14.3 dm which is taller than commonly found in other types of Agapanthus plants.

Rhizome: Cylindrical, branched, with many fleshy roots.

FOLIAGE

General: The leaves are numerous, arising from near the ground, erect to somewhat spreading, and united at the base into a short pseudo-stem.

Size: Mature leaves reach a maximum length of 6.5 dm. and may reach a width of 4–5 cm.

Color: The upper and lower surfaces are slightly dull medium green (Green Group 143) with the extreme margins being translucent pale green (Green Group 143C).

Shape: The leaves are strap-shaped (lorate), deeply channeled below grading to shallowly channeled above.

Venation: Apparent above, conspicuous below leaf blade. Veins closely spaced, about 2 mm apart near the center of blade becoming progressively more closely spaced toward margins.

Arrangement: The leaves are distichously arranged.

Texture: The texture of the leaves are thick-textured but pliable and not brittle, softer and sometimes hanging in the uppermost ¼ to ⅓. Torn leaf portions bear long streaming fibers.

INFLORESCENCE

Arrangement: Flowers are numerous, crowded in false umbels atop tall, slender scapes emerging from the center of the leaves and much exceeding them in height.

Umbel: To 22 cm across and 16 cm high.

Scapes: Scapes slender, glaucescent, and are more or less rounded in cross section, reaching a maximum height of 12 dm. About 16 mm thick at the base and 8 mm thick at apex.

Bracts: Inflorescence subtended by thin bracts which soon dry and fall away leaving a conspicuous broad corky scar at the top of the scape.

FLOWERS

General: Flowers hypogynous, long-pedicillate, very numerous, out-facing to having a declination of approximately 40 degrees to the stem, infundubular-salverform, slightly zygomorphic, from a cylindrical base about 12–13 mm long.

Buds: Narrowly oblanceolate in outline.

Dimensions: Individual flowers range from 3.3–3.8 cm long and 3.5–3.9 cm across at the apex when fully expanded.

Pedicels: Each flower in the inflorescence is borne on a thin pedicel ranging in length from 6.5–6.8 cm.

Tepals: Each flower is composed of six segments arranged in two whorls of three, a narrower outer trio and a broader inner trio. These are flaring or slightly reflexed, mostly free or touching along the edges, rarely slightly overlapping, Pigmentation: Tepals with prominent dark (Violet-Blue Group 93A) midribs ventrally from the apex becoming pale at the base of the tube. Extreme margins or edges ventrally equally deeply pigmented. Lowest ½ to ¾ within whitish between darker margins and midveins, grading to medium violet-blue (Violet-Blue Group 94A) above. Ventral surfaces are more evenly colored.

Outer segments: Narrowly oblanceolate, with raised midrib at dorsal apex forming a heavy mucro, apical margin white-fimbriate, 3.7–3.9 cm long and 7–8 mm wide.

Inner segments: Spathulate-oblanceolate, 3.6–3.7 cm long and 10–11 mm wide.

Stamens: Six, adnate to the floral tube, declinate along lowest tepal, shorter than or equaling tepals. Filaments medium violet-blue (Violet-Blue Group 94A) above, white at base. Pollen yellow, anthers later black.

Pistil: Style includes in corolla, declinate without defined stigma, shorter than or equaling the shortest filament, pale violet-blue (Violet-Blue Group 94A) above, white below, about 2.0–2.1 cm long. Ovary greenish-yellow, trigonous, 8.5–9.0 mm long by 3 mm broad at apex.

Fruits: Not seen.

I claim:

1. A new and distinct variety of Agapanthus plant substantially as shown and described characterized by its ability to reach a height of 14.3 dm when in flower which includes slender glaucesent scapes that reach to a maximum height of 12 dm having a hardy upright growth habit along with prominent dark blue-violet flowers being slightly zygomorphic from the cylindrical base and with each flower being composed of six segments arranged in two whorls of three defined by a narrower outer pair, wherein the flowers range from 3.3 to 3.8 cm long and 3.5 to 3.9 cm across at the apex when fully expanded, with leaves being formed having veins closely spaced about 2 mm apart near the center of the leaves which are thick-textured but pliable and reach a maximum length of 6.5 dm having a width of 4 to 5 cm.

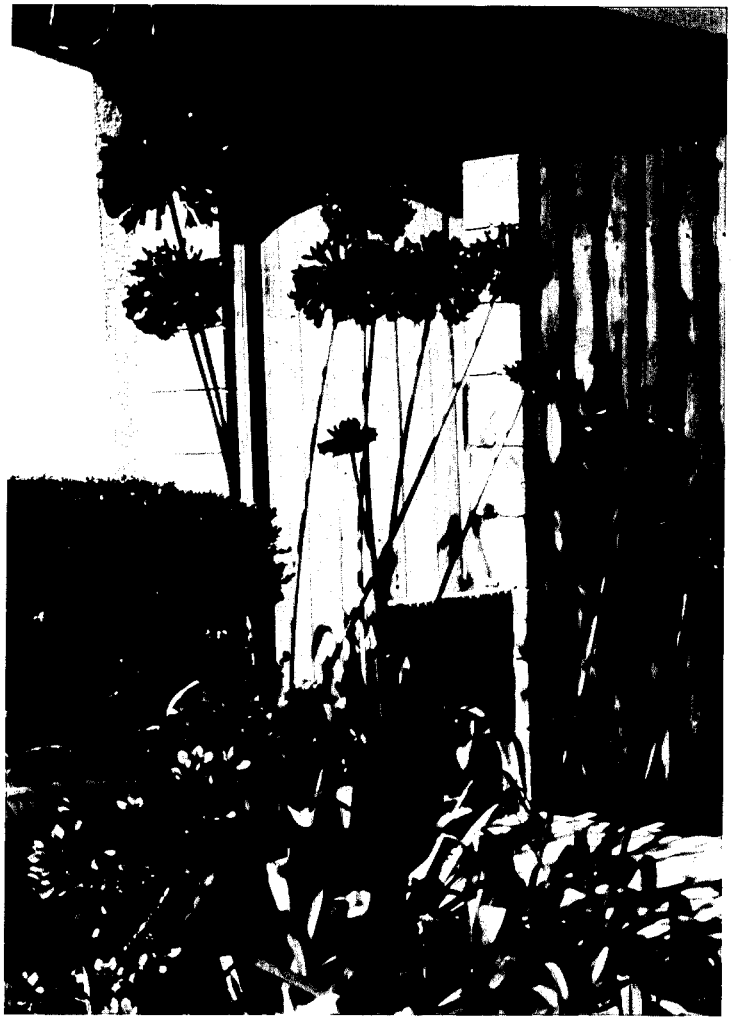

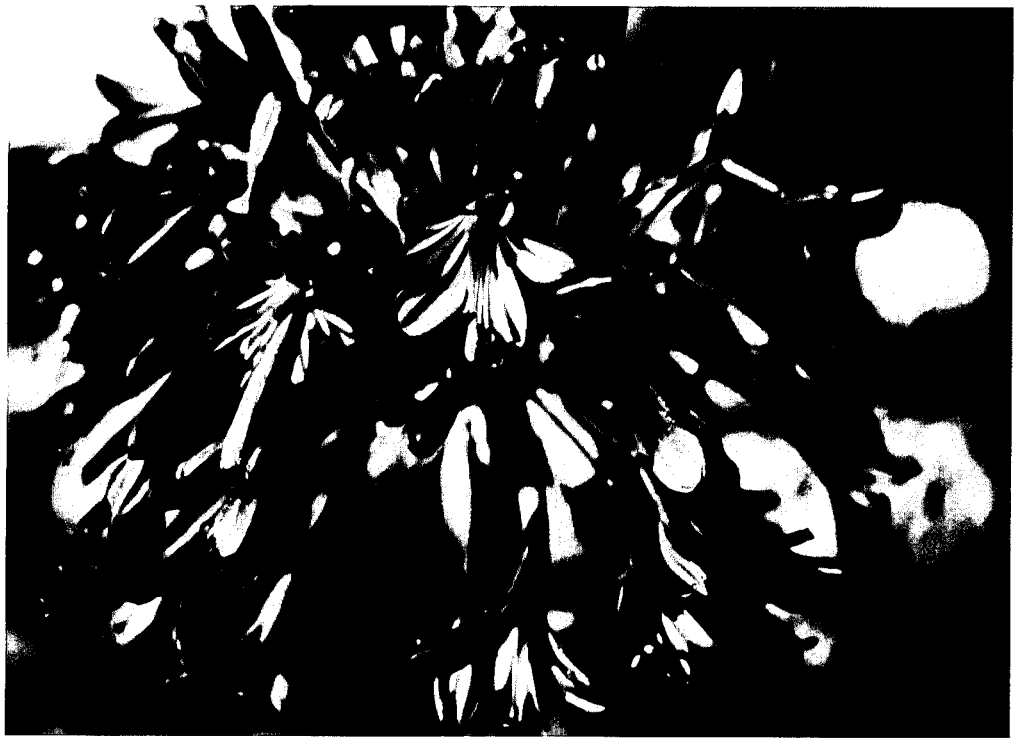

* * * * *